US010226191B2

(12) United States Patent
Kim

(10) Patent No.: US 10,226,191 B2
(45) Date of Patent: Mar. 12, 2019

(54) NEWBORN HEART RATE MONITOR

(71) Applicant: The Regents of the University of California, Oakland, CA (US)

(72) Inventor: Jae H. Kim, Poway, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1164 days.

(21) Appl. No.: 14/354,114

(22) PCT Filed: Oct. 24, 2012

(86) PCT No.: PCT/US2012/061728
§ 371 (c)(1),
(2) Date: Apr. 24, 2014

(87) PCT Pub. No.: WO2013/063144
PCT Pub. Date: May 2, 2013

(65) Prior Publication Data
US 2014/0276148 A1    Sep. 18, 2014

Related U.S. Application Data

(60) Provisional application No. 61/550,574, filed on Oct. 24, 2011.

(51) Int. Cl.
*A61B 17/122* (2006.01)
*A61B 5/00* (2006.01)
*A61B 5/024* (2006.01)

(52) U.S. Cl.
CPC ........ *A61B 5/02444* (2013.01); *A61B 5/6813* (2013.01); *A61B 5/7203* (2013.01);
(Continued)

(58) Field of Classification Search
CPC ... A61B 5/02444; A61B 5/746; A61B 5/7405; A61B 5/742; A61B 5/7203; A61B 5/6813; A61B 5/6838; A61B 2562/0261
See application file for complete search history.

(56) References Cited

U.S. PATENT DOCUMENTS 3,573,394 A *   4/1971   Birnbaum ................ H04R 1/46
                                                   310/331
3,978,849 A *   9/1976   Geneen .................. A61B 5/024
                                                   600/503
(Continued)

FOREIGN PATENT DOCUMENTS

JP      2002-224051 A     8/2002
JP      2010-534091 A    11/2010
KR   10-2008-0082294 A    9/2008

OTHER PUBLICATIONS

WO 2013/063144 A1, International Search Report, dated Jan. 28, 2013.

*Primary Examiner* — Tiffany Weston
(74) *Attorney, Agent, or Firm* — Stuart H. Mayer; Mayer & Williams PC

(57) ABSTRACT

A newborn heart rate monitor is disclosed comprising a sensor integrated into a clamp configured to clamp onto the umbilical cord of a newborn infant. The sensor is configured to detect radial pulsation of the umbilical cord and produce a corresponding electrical signal which can be processed by a processor to calculate the heartbeat of the newborn infant. The heartbeat can be displayed visually or audibly or both. A second reference sensor can be included to detect environmental noise and the processor can be configured to use the detected environmental noise to filter noise from the detected heartbeat. Additional filtering, processing, and alert algorithms can be included for processing and analyzing the detected heartbeat data.

10 Claims, 2 Drawing Sheets

(52) U.S. Cl.
CPC ............ *A61B 5/742* (2013.01); *A61B 5/7405* (2013.01); *A61B 5/746* (2013.01); *A61B 5/6838* (2013.01); *A61B 17/122* (2013.01); *A61B 2562/0261* (2013.01)

(56) References Cited

U.S. PATENT DOCUMENTS

| | | | | |
|---|---|---|---|---|
| 4,685,464 | A * | 8/1987 | Goldberger | A61B 5/14552 600/344 |
| 7,402,164 | B2 * | 7/2008 | Watson, Jr. | A61B 17/122 606/120 |
| 8,641,613 | B2 * | 2/2014 | Coelho | A61B 5/0205 600/120 |
| 2007/0276273 | A1 * | 11/2007 | Watson, Jr. | A61B 5/0006 600/391 |
| 2008/0294058 | A1 * | 11/2008 | Shklarski | A61B 5/02055 600/502 |
| 2009/0163776 | A1 | 6/2009 | Inbar | |

* cited by examiner

NEWBORN HEART RATE MONITOR

BACKGROUND

The present invention relates generally to the field of heart rate monitoring devices and, more specifically, heart rate monitoring devices designed to monitor the heart rate of a newborn infant.

Currently, there are few methods of capturing the heart rate.

The first few minutes of life after birth is a critical time when dramatic physiologic changes take place to prepare an infant for the outside world. Often, some term and many premature neonates are born with complications that require immediate resuscitation to survive. The neonate heart rate is one of the key physiologic metrics doctors use for determining whether or not the resuscitation effort is working. Because the infant's heart rate is so important, an accurate, instantaneous representation of the heart rate can be crucial. Current methods require manual palpation of the pulsating umbilical cord or listening to (auscultation) with a stethoscope for heart beats, both of which are prone to inaccuracy and human error particularly in situations of high stress and in the presence of external stimuli or noises. Furthermore, these methods complicate the delivery room working area by increasing the number of bodies. Conventional pulse oximetry and electro-cardiograms also suffer from disadvantages due to respective signal delay (between 1 and 3 minutes) or difficulty with application. A device that can automatically capture the neonate heart rate immediately and accurately to the resuscitation team after birth and provide real time audio and visual feedback, could improve the quality of resuscitation offered and ensure that critical time sensitive decisions are made.

Current delivery room practices are not consistently accurate for the monitoring of the newborn heart rate. Most newborns are assessed at birth for a normal heart rate using one of three different methods. The first and simplest is the palpation of the umbilical cord with the hand. Manual palpation of the umbilical cord requires medical team members to sense the pulse and communicate it, using their fingers in a fashion similar to a metronome. Manual palpation requires significant clinical experience, but even then, experienced professionals are prone to critical errors.

The second method is auscultation. While auscultation is typically a good method for hearing heart sounds, the delivery room environment is often prone to excessive external stimuli and noises that can distract the listener from hearing the heart beats. The most common of these errors is either a miscount, where faint heartbeats are not sensed and therefore not relayed to the attending medical team, or double counts, where the atrial and ventricular systoles are counted as individual heartbeats rather than part of the same beat. It has been observed in some cases, using video recording of delivery room resuscitation, that a heart rate readout from a delivery room team member is not consistent with the simultaneous oxygen saturation or ECG monitor.

The third method of monitoring heart rate, which is less commonly used than the first two, is pulse oximetry. The advantage of pulse oximetry is that it is noninvasive and extremely accurate, providing information not only on heart rate, but blood oxygenation as well. Unfortunately, pulse oximetry devices can sometimes require 2-3 minutes of initial data collection to establish a patient's baseline, creating a "blackout window" during which they are ineffective. This has been most frequent in smaller preterm infants, which is disadvantageous since they are generally a sicker patient group. Therefore, while patients in stable condition or under observation are typically not hampered by this minor inconvenience, in neonates that are preterm and/or in respiratory distress or with other complications, a two minute "black window" can be a significant disadvantage.

Existing electrocardiographic technology is not easily suited for placement into the delivery room. The most reliable detection of heart rate is usually the placement of chest electrodes attached to an electrocardiogram (ECG) machine but two factors make it challenging to easily incorporate this. The first is the sticking of electrodes onto a newborn's skin. Freshly born infants have skin that is wet and often covered with vernix. Both conditions can make sticking of electrodes difficult. The second problem is the bulkiness of typical ECG machines and cumbersomeness of the leads. Most delivery rooms do not have the space or capacity to provide machines in all the different delivery areas such as labor rooms, operating rooms, and resuscitation rooms. A portable device for accurately measuring a neonates heart rate would be helpful in emergency situations where other team members are scarce and when such a device could be carried readily in transport.

SUMMARY

One embodiment of the invention relates to a neonatal heart rate monitoring unit comprising: jaws configured to clamp an umbilical cord; a sensor embedded in at least one of the jaws configured to be deflected by pulsations of the umbilical cord; and a visual indicator positioned on at least one of the jaws for indicating a deflection of the sensor.

Another embodiment of the invention relates to a heart rate monitoring unit comprising: a clamp configured to be attached to an umbilical cord; a heartbeat sensor operably connected to the clamp placing the heartbeat sensor in contact the umbilical cord when the claim is attached to the umbilical cord, the heartbeat sensor configured to detect radial pulsation of the umbilical cord with each heartbeat; a processor for converting the detected radial pulsation into heartbeat data; and an indicator for communicating the heartbeat data.

The heartbeat sensor may further comprise a piezo-film sensor which in response to being bent with each radial pulsation of the umbilical cord produces an electrical response indicative of heart rate. The heartbeat sensor may further comprise a silicone bed configured to facilitate sensor deflection and increase the electrical response indicative of heart rate.

The heart rate monitoring unit may further comprise an amplifier for further amplifying the electrical response.

The heart rate monitoring unit may further comprise an integrated filter for filtering noise from the electrical response.

The heart rate monitoring unit may further comprise a reference sensor configured to detect environmental noise and produce an electrical response indicative of environmental noise, wherein the processor uses the electrical response indicative of environmental noise to remove environmental noise from the electrical response of the heartbeat sensor.

The indicator may be a light emitting diode configured to visual signal indicative of the heartbeat data.

The indicator may be a speaker configured to produce an audio signal indicative of the heartbeat data.

The heart rate monitoring unit may further comprise a battery for powering the unit.

The processor may further comprise an adjustable peak detection algorithm for detecting peaks in the electrical response of the heartbeat sensor.

The heart rate monitoring unit may further comprise an alarm system configured to detect and report heartbeat data above and/or below preset threshold values.

The indicator may further comprise a display for displaying a numeric value indicative of the heartbeat data.

DETAILED DESCRIPTION OF THE ONE EMBODIMENT

The following detailed description is of one possible embodiment of the invention. The description should not be taken in a limiting sense, but is made merely for the purpose of illustrating the general principles of the invention. Broadly, an embodiment of the present invention generally provides a thin-film piezo-electric sensor integrated into an easily attachable, compact monitoring unit that clips to the umbilical cord of a newborn infant.

Figure 1:
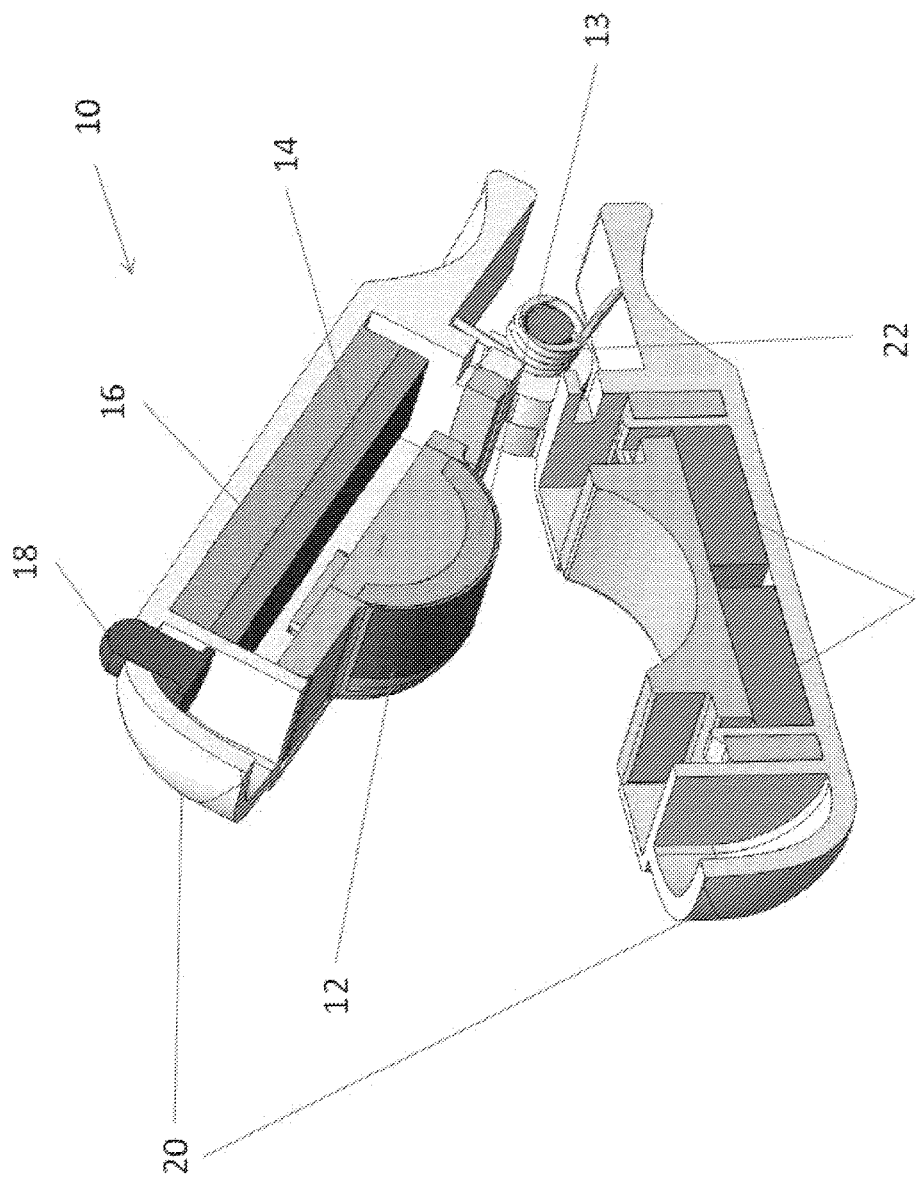
FIG. 1 is a perspective view of one embodiment of a heart rate monitoring unit.

Referring now to FIG. 1, an exemplary embodiment of a monitoring unit 10 which may be attached to an umbilical cord close to a neonate's abdomen directly after birth is shown. In operation, with each heartbeat, radial pulsation of the umbilical cord may bend an integrated piezo-sensor 12. Bending of the sensor 12 may cause quartz crystals within a piezo-film to rearrange and produce a slight voltage. The sensor 12 may rest on a compliant silicone bed 13 to facilitate sensor deflection and increase its electrical response. Gain for voltage output of the sensor 12 may be provided with a surface mounted charge amplifier 14. A microcontroller 16 may mitigate noise with the integrated filter (not shown).

Immediately after attachment of the unit 10 to an umbilical cord, the microcontroller 16 may begin to signal a built-in indicator LED 18 to flash with each pulsation of the umbilical cord. Additionally a speaker (not shown) may be provided to produce sounds that correspond to flashes of the LED 18 so that audiovisual feedback of the heart rate may be instantly provided to an attending medical team, improving response time, thereby increasing each infant's chance of survival.

The monitoring unit 10 may be advantageously configured as a clothespin type clamp that may optimally interface with the umbilical cord. Various configurations of jaws 20 may be employed, including angled, flat, and concave jaws. The jaws 20 may be designed to securely attach and provide maximum surface mounting area for the thin-film piezo-sensor 12. A torsion spring 22 may provide clamping force for the jaws 20. Electrical power for the unit may be provided with one or more batteries 24.

Use of the clamp design may be advantageous because it may provide for speed and ease of attachment. Also, the clamp design may provide two shells in which to place all the internal components of the monitoring unit 10. This may potentially reduce the width of the design by placing the umbilical cord in the center of the unit 10 as opposed to on a single side. Attaching the cord in the center of the heart rate monitoring unit 10 may help balance the weight of the unit on the neonate. With two relatively large contact surface areas, the clamp design may provide two possible places for either single or multiple sensor use.

The sensor 12 may be chosen for its precision and ruggedness, as well as its ability to reject 60 Hz interference. Each transduced heartbeat may result in a 10-20 mV signal. This signal may be filtered to remove any remaining high-frequency noise, and then amplified. A resulting waveform may be fed through the microprocessor 16 using an adjustable peak detection algorithm. A detected peak may be used to signal a turn-on of the LED 18 for each beat of the neonate's heart.

In an exemplary embodiment, the monitoring unit 10 may utilize two sensors; the sensor 12 that interfaces with the umbilical cord and transduces the heartbeat; and a second reference sensor (not shown) that may be mounted internally within the monitoring unit 10. This reference sensor may detect gross movements of the baby as well as any outside noise, acting in a manner similar to a noise canceling microphone. A signal from the reference sensor may be subtracted from the umbilical sensor 12, and a combined sensor signal may be filtered to remove any remaining noise, and then amplified. The microprocessor 16 may analyze the combined sensor signal, and determine whether it represents a heartbeat or residual noise. If the signal is above a level preset for a heartbeat, the algorithm may trigger audio and visual feedback.

In an exemplary embodiment, the amplifier circuit 14 may utilize a three-pole low pass filter amplifier circuit which may filter at a frequency of about 12-13 Hz and may prevent AC line interference. DC gain may be about +30 dB, which may produce peaks of about 100 mV per heartbeat. The circuit 14 may consume less than 100 µA of current. The microprocessor 16 may be an MSP430, available from Texas Instruments. The MSP430 may possess key features such as ultra-low power modes which may save overall power consumption yet still allow fully functional programmable electronics. The MSP430 may also provide numerous peripherals for various output applications to accommodate audiovisual feedback; and may also feature a 16-bit RISC CPU which may result in a desirably fine resolution for precise signal acquisition. In addition, various different control, filtering, processing, and analyzing processes can be implemented as software configured to run on the MSP430.

Figure 2:
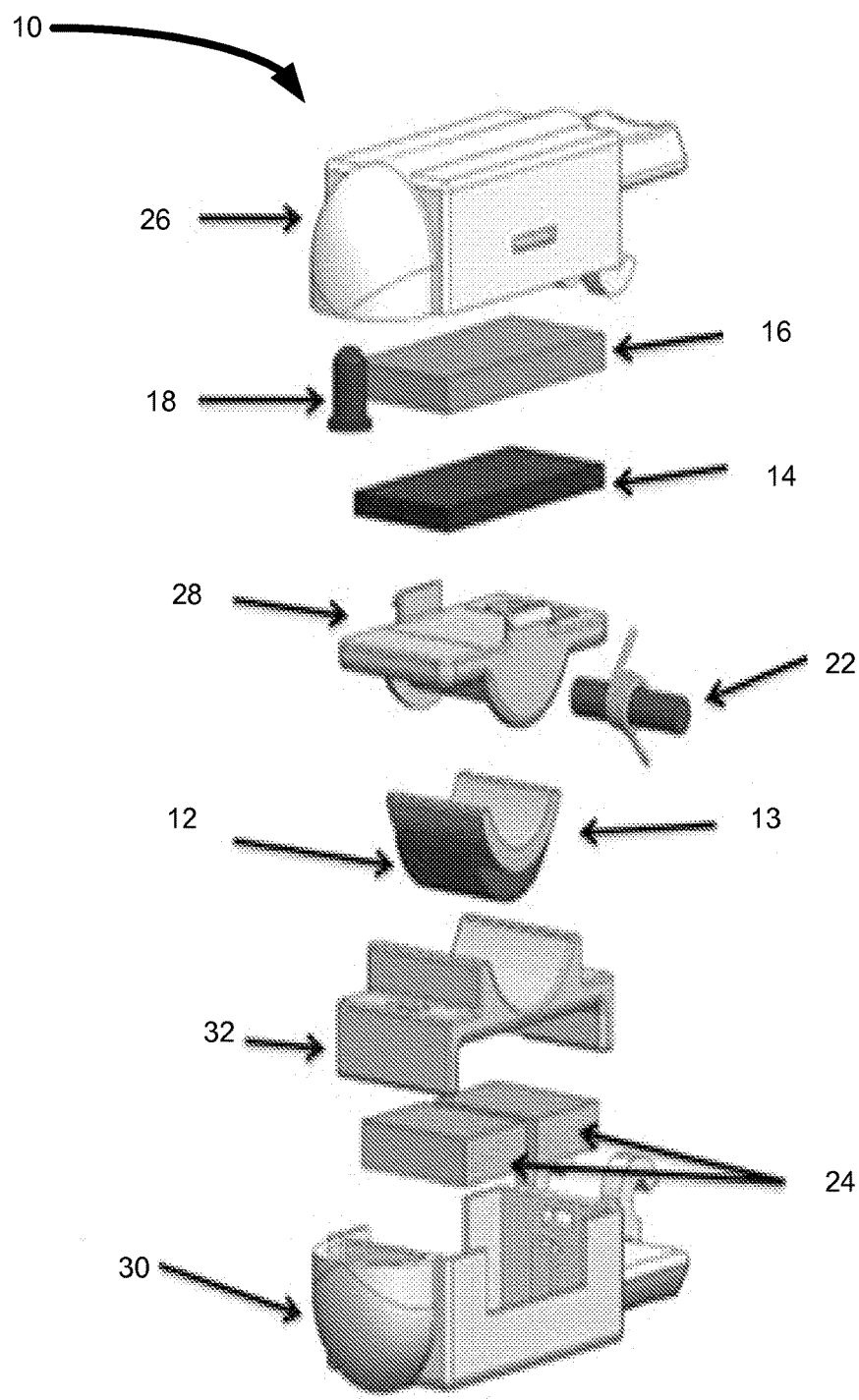
FIG. 2 is an exploded view of one embodiment of the heart rate monitoring unit of FIG. 1.

FIG. 2 illustrates an exploded view of one embodiment of the heart rate monitoring unit 10 of FIG. 1. As described above, the monitoring unit 10 can be configured as a clothespin-type clamp with jaws that may optimally interface with the umbilical cord of a newborn infant. Also as described above and as shown in FIG. 2, the jaws 20 may be configured to provide two shells in which to place the internal components of the monitoring unit 10. The two shells can comprise a top housing 26 and top insert 28 configured to form a top shell and a bottom housing 30 and bottom insert 32 configured to form a bottom shell. The top housing 26 and top insert 28 can be configured to be fit together to form the hollow top shell and the bottom housing 30 and bottom insert 32 can be configured to fit together to form the hollow bottom shell. As shown, the amplifier 14, microprocessor 16 and LED 18 can be housed in the top shell between the top housing 26 and top insert 28 and the batteries 24 can be housed in the bottom shell between the bottom housing 30 and bottom insert 32. The top housing 26 can include an opening through which the LED 18 can protrude so that it is visible on the outside of the monitoring unit 10. The silicone bed 13 and piezo-sensor 12, can be secured to the underside of the top insert 28 so that when assembled as a clamp and when clamped on the umbilical cord of a newborn infant, the sensor 12 interfaces with the umbilical cord to sense and measure the radial pulsation of the umbilical cord with each heartbeat of the newborn infant. The torsion spring 22 can be connected between the top housing 26 and bottom housing 30 to form the clamp and to provide clamping force securing the monitoring unit 10 to the umbilical cord.

This embodiment of the monitoring unit 10 can sense the pulsating umbilical cord by the described external clamping mechanism. The thin-film piezoelectric sensor 12 and silicone bed 13 can be operably connected to the microprocessor 16 to provide input to the microprocessor 16 indicative of the heart rate of the newborn infant. Any number of jaw attachment concepts can be used, including angled, flat, and concave jaws. The jaws of the clamp can be designed to securely attach and provide maximum surface mounting area for the thin-film piezo sensor 12, which rests on the compliant silicone bed 13 to facilitate sensor deflection and increase its electrical response. As described above, the thin-film sensor 12 can provide precision and ruggedness, as well as an ability to reject 60 Hz interference from the mains due to coaxial cables. Each transduced heartbeat can result in a 10-20 mV signal.

This transduced heartbeat signal can further be filtered to remove any remaining high-frequency noise, and amplified. The resulting waveform can be fed through the microprocessor 16 using an adjustable peak detection algorithm, which can be configured to identify the larger of the two distinct peaks. The peaks can turn on the LED 18 corresponding to each beat of the neonate's heart.

The monitoring unit 10 can be attached to the umbilical cord close to the neonate abdomen directly after birth. With each heartbeat, the radial pulsation of the cord bends the integrated sensor 12. The sensor 12 bend causes the quartz crystals within the piezo-film silicone bed 13 to rearrange and produce a slight voltage. This voltage can be gained with the surface mounted charge amplifier 14, and the noise can be mitigated with an integrated filter. Immediately after attachment, the microcontroller (FIG. 4) signals the built-in LED to flash with each pulsation. Meanwhile, the algorithm runs to determine the ideal threshold for peak detection from the current processed signal. Numerous different designs can be used to increase the signal-to-noise ratio for the monitoring unit 10 to function properly for all possible size of umbilical cords. Attachment and sensor placement can further be optimized for the monitoring unit 10 to accurately monitor the heart rate. As a result, umbilical cords with different wall thicknesses, diameters, pulse rates, and pulse magnitudes can be accommodated.

As described above, embodiments of the invention can use pressure transduction to detect palpations in the umbilical cord of a neonate to report heart rate and pulsatility strength. Embodiments can provide immediate (within seconds) detection of heart rate and can couple the monitor and umbilical clamp function into one device. There is a potential for making the monitor removable so that the physical clamp can be left behind on the umbilical cord after the monitoring function is no longer necessary or desired. Embodiments provide for the quantification of strength of the pulsations as a measure of blood pressure or cardiac output and visual and audible signal indicators of heart rate can be provided freeing additional manual support for heart rate detection and reporting. The monitoring unit can include additional features such as a display for displaying the actual numeric heart rate as well as visual and/or audible alarms that trigger further assessment by the attending medical resuscitation team based on the heart rate and pulsatility strength.

As described, the monitoring unit can be associated or coupled with umbilical cord clamp functionality. It can be made of light weight material to prevent tugging and tension on the umbilical cord and can include a small power source either in the form of a cell or battery or alternative energy storage device that does not require chemicals such as a spring. The monitoring unit can be configured to detect pulsations using a thin-film piezo-electric sensor that wraps against the umbilical cord. The unit can adjust to varying sizes of the umbilical cord from preterm to term infant size ranges and beyond to equally transduce the pulsatility signal. The unit can be configured to filter the pulsatile signal to remove any movement artifact and electrical noise and to transduce the signal into a generated numeric heart rate for visual and audio display. The visual display may include actual heart rate values. The unit may also include an alarm system that reports when the heart rate and pulsatility are below normal values and require further assessment or resuscitative measures to the medical team. These features can be implemented in software loaded in the microprocessor. Circuits and microprocessors can be used to process the signal on-board and allow the monitoring unit to operate as a standalone device, eliminating the need for connections to external equipment. The unit can include a spring loaded in the clamp hinge to provide tension over the sensor and an additional clamping mechanism can also be included adjacent to provide complete and permanent cord clamping. Material can be provided on the interior to prevent slippage of the wet umbilical cord. In one embodiment, this may be in the form of a roughened surface or additional materials with high friction value on wet surfaces.

As described above, one embodiment of a neonatal heart rate monitor can include a thin piezo film sensor, a low pass filter/amplification circuit, a microprocessor, and the device housing. One suitable thin-film piezo-sensor is manufactured by Measurement Specialties and distributed by Elotek. This sensor behaves much like a dynamic strain gauge in that when deformed a voltage is created which is proportional to the volume of film stressed. As such, each systolic and diastolic beat from the neonate can be transduced by the sensor and the corresponding voltages sent to be filtered and amplified.

In one embodiment, a three-pole low pass filter amplifier circuit which filters at a frequency of 12-13 Hz and prevents AC line interference can be used. The DC gain can be about +30 dB, which gave peaks of about 100 mV per heart beat. In one embodiment, such an amplifier circuit can consume just less than 100 µA of current. Once the signal is filtered and amplified, the peak detection algorithm loaded onto the microprocessor can process the signal and send out the corresponding audio and visual feedback. As described above, one embodiment of the invention can use the MSP430 microprocessor, by Texas Instruments. This microprocessor features ultra-low power modes which can save on overall power consumption yet still allowing fully functional programmable electronics. It can also provided numerous peripherals for various output applications to accommodate for a feedback system which can be included. The MSP430 also featured a 16-bit RISC CPU which can produce fine resolution for precise signal acquisition.

The housing can be designed such that optimal sensor placement and ease of application is accomplished. A clamp like structure can be utilized because it allows an operator to quickly and single handedly apply the sensor on the neonate.

Finger tabs with small indents allow for snug grasping and pinching of the device. One suitable spring element for closing the clamp can include a 5 in-lb torsion spring. A curved geometry of an area for sensor placement can be designed to enable the maximum force from the cord to be translated onto the sensor. A silicone backing can be used to mount the sensor to the device in order to create a compliant backing, which can result in a better acquired signal. While one embodiment of the invention described herein uses a piezoelectric sensor, other types of sensors may be suitable, such as bend sensors, infrared sensors, ultrasound sensors, and/or pressure sensors.

The various diagrams may depict an example architectural or other configuration for the various embodiments, which is done to aid in understanding the features and functionality that can be included in the invention. The present disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

It should be understood that the various features, aspects and functionality described in one or more of the individual embodiments are not limited in their applicability to the particular embodiment with which they are described, but instead can be applied, alone or in various combinations, to one or more of the other embodiments of the present disclosure, whether or not such embodiments are described and whether or not such features are presented as being a part of a described embodiment. Thus, the breadth and scope of the present disclosure should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

Moreover, various embodiments described herein are described in the general context of method steps or processes, which may be implemented in one embodiment by a computer program product, embodied in, e.g., a non-transitory computer-readable memory, including computer-executable instructions, such as program code, executed by computers in networked environments. A computer-readable memory may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

As used herein, the term module can describe a given unit of functionality that can be performed in accordance with one or more embodiments of the present invention. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality. Where components or modules of the invention are implemented in whole or in part using software, in one embodiment, these software elements can be implemented to operate with a computing or processing module capable of carrying out the functionality described with respect thereto. The presence of broadening words and phrases such as "one or more," "at least," "but not limited to" or other like phrases in some instances shall not be read to mean that the narrower case is intended or required in instances where such broadening phrases may be absent.

What is claimed is:
1. A heart rate monitoring unit, comprising:
 a clamp configured to be attached to an umbilical cord, wherein the clamp is of a clothespin type and includes a top jaw and a bottom jaw biased together by a torsion spring and configured to clamp the umbilical cord, wherein inner surfaces of the jaws comprise curved geometries that fit together, and wherein the clamp provides a clamping force securing the clamp to the umbilical cord;

a bed layer coupled to at least one of the inner surfaces of the jaws:

a heartbeat sensor operably connected to the bed layer placing the heartbeat sensor in contact with the umbilical cord when the clamp is attached to the umbilical cord, the heartbeat sensor configured to detect radial pulsation of the umbilical cord with each heartbeat, the bed layer facilitating deflection of the heartbeat sensor, the bed layer further comprising a silicone bed configured to facilitate sensor deflection and increase the electrical response indicative of heart rate, and wherein the heartbeat sensor further comprises a piezo-film sensor which in response to being bent with each radial pulsation of the umbilical cord produces an electrical response indicative of heart rate;

a processor for converting the detected radial pulsation into heartbeat data; and an indicator for communicating the heartbeat data.

2. The unit of claim 1, further comprising an amplifier for further amplifying the electrical response.

3. The unit of claim 1, wherein the processor further comprises an integrated filter for filtering noise from the electrical response.

4. The unit of claim 1, further comprising a reference sensor configured to detect environmental noise and produce an electrical response indicative of environmental noise, wherein the processor uses the electrical response indicative of environmental noise to remove environmental noise from the electrical response of the heartbeat sensor.

5. The unit of claim 1, wherein the indicator is a light emitting diode configured to produce a visual signal indicative of the heartbeat data.

6. The unit of claim 1, wherein the indicator is a speaker configured to produce an audio signal indicative of the heartbeat data.

7. The unit of claim 1, further comprising a battery for powering the unit.

8. The unit of claim 3, wherein the processor further comprises an adjustable peak detection algorithm for detecting peaks in the electrical response of the heartbeat sensor.

9. The unit of claim 1, further comprising an alarm system configured to detect and report heartbeat data above and/or below preset threshold values.

10. The unit of claim 1, wherein the indicator further comprises a display for displaying a numeric value indicative of the heartbeat data.

* * * * *